United States Patent
Thompson et al.

(10) Patent No.: US 12,237,617 B2
(45) Date of Patent: *Feb. 25, 2025

(54) CONNECTION SYSTEM FOR ESTABLISHING AN ELECTRICAL CONNECTION THROUGH A DRAPE AND METHODS THEREOF

(71) Applicant: Bard Access Systems, Inc., Salt Lake City, UT (US)

(72) Inventors: Chase Thompson, Bountiful, UT (US); Jerry Zhao, Salt Lake City, UT (US); Bradley W. Zentgraf, West Jordan, UT (US); Jason R. Stats, Layton, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/539,518

(22) Filed: Dec. 14, 2023

(65) Prior Publication Data
US 2024/0170887 A1    May 23, 2024

Related U.S. Application Data

(63) Continuation of application No. 17/240,826, filed on Apr. 26, 2021, now Pat. No. 11,936,132, which is a
(Continued)

(51) Int. Cl.
*H01R 13/52* (2006.01)
*A61B 46/00* (2016.01)
(Continued)

(52) U.S. Cl.
CPC ......... *H01R 13/5224* (2013.01); *A61B 46/00* (2016.02); *A61M 25/0102* (2013.01);
(Continued)

(58) Field of Classification Search
CPC ............ H01R 13/5224; H01R 13/5219; H01R 13/04; H01R 13/631; H01R 13/7175;
(Continued)

(56) References Cited

U.S. PATENT DOCUMENTS 2,831,174 A    4/1958 Hilmo
2,959,766 A    11/1960 Jacobsen
(Continued)

FOREIGN PATENT DOCUMENTS

EP    1318576 A1    6/2003
EP    3270817 A1    1/2018
(Continued)

OTHER PUBLICATIONS

"Sampling Accessories" Spectrometers Accessories Catalogue, pp. 71-102, XP055014465, retrieved from the Internet URL: http//www.mikropack.de/d/specto/pdfy-downoads/sampling accessories. pdf, Jan. 1, 2004 (Jan. 1, 2004).
(Continued)

*Primary Examiner* — Gary F Paumen
(74) *Attorney, Agent, or Firm* — Rutan & Tucker LLP

(57) ABSTRACT

A connection system includes a first connector and a second connector configured for establishing one or more electrical connections through a drape. The first connector can include an alignment protrusion and a first piercing element having one or more electrical contacts configured to pierce the drape. The second connector can include an alignment notch, a channel, and a first receptacle configured to receive the first piercing element when inserted therein. The alignment notch can be configured to accept the alignment protrusion when the first connector is aligned with the second connector then disposed over the second connector. The channel can be configured to allow the alignment protrusion to slide along a length of the second connector.
(Continued)

The first receptacle can have one or more electrical contacts configured to form at least a first electrical connection of the one or more electrical connections with the first connector.

14 Claims, 9 Drawing Sheets

Related U.S. Application Data continuation of application No. 16/261,368, filed on Jan. 29, 2019, now Pat. No. 10,992,078.

(60) Provisional application No. 62/623,394, filed on Jan. 29, 2018.

(51) Int. Cl.
  *A61M 25/01*   (2006.01)
  *H01R 4/2406*  (2018.01)
  *H01R 13/04*   (2006.01)
  *H01R 13/631*  (2006.01)
  *H01R 13/717*  (2006.01)

(52) U.S. Cl.
  CPC ....... *A61M 25/0111* (2013.01); *H01R 4/2406* (2018.01); *H01R 13/04* (2013.01); *H01R 13/631* (2013.01); *H01R 13/7175* (2013.01); *A61M 2025/0166* (2013.01); *H01R 2201/12* (2013.01)

(58) Field of Classification Search
  CPC .... H01R 4/2406; H01R 4/24; H01R 2201/12; A61B 46/00; A61M 25/0101; A61M 25/0111; A61M 2025/0166
  See application file for complete search history.

(56) References Cited

U.S. PATENT DOCUMENTS

| | | |
|---|---|---|
| 3,329,928 A | 7/1967 | Broske |
| 3,532,095 A | 10/1970 | Miller et al. |
| 3,597,582 A | 8/1971 | Goode et al. |
| 3,605,743 A | 9/1971 | Olvera |
| 3,649,952 A | 3/1972 | Harmon |
| 3,665,372 A | 5/1972 | Goode et al. |
| 3,673,548 A | 6/1972 | Mattingly, Jr. et al. |
| 3,746,814 A | 7/1973 | Lackey et al. |
| 3,824,556 A | 7/1974 | Berkovits et al. |
| 3,842,394 A | 10/1974 | Bolduc |
| 4,200,348 A | 4/1980 | Stupay |
| 4,220,387 A | 9/1980 | Biche et al. |
| 4,254,764 A | 3/1981 | Neward |
| 4,303,293 A | 12/1981 | Grunwald |
| 4,369,794 A | 1/1983 | Furler |
| 4,490,003 A | 12/1984 | Robinson |
| 4,614,395 A | 9/1986 | Peers-Trevarton |
| 4,632,121 A | 12/1986 | Johnson et al. |
| 4,700,997 A | 10/1987 | Strand |
| 4,702,256 A | 10/1987 | Robinson et al. |
| 4,761,143 A | 8/1988 | Owens et al. |
| 4,858,810 A | 8/1989 | Intlekofer et al. |
| 4,860,742 A | 8/1989 | Park et al. |
| 4,973,329 A | 11/1990 | Park et al. |
| 5,159,861 A | 11/1992 | Anderson |
| 5,178,159 A | 1/1993 | Christian |
| 5,217,435 A | 6/1993 | Kring |
| 5,325,746 A | 7/1994 | Anderson |
| 5,325,868 A | 7/1994 | Kimmelstiel |
| 5,334,045 A | 8/1994 | Cappa et al. |
| 5,354,326 A | 10/1994 | Comben et al. |
| 5,407,368 A | 4/1995 | Strand et al. |
| 5,423,877 A | 6/1995 | Mackey |
| 5,437,277 A | 8/1995 | Dumoulin et al. |
| 5,454,739 A | 10/1995 | Strand |
| 5,482,038 A | 1/1996 | Ruff |
| 5,489,225 A | 2/1996 | Julian |
| 5,501,675 A | 3/1996 | Erskine |
| 5,538,444 A | 7/1996 | Strand et al. |
| 5,560,358 A | 10/1996 | Arnold et al. |
| 5,591,119 A | 1/1997 | Adair |
| 5,624,281 A | 4/1997 | Christensson |
| 5,685,855 A | 11/1997 | Erskine |
| 5,752,915 A | 5/1998 | Neubauer et al. |
| 5,766,042 A | 6/1998 | Ries et al. |
| 5,769,786 A | 6/1998 | Wiegel |
| 5,797,880 A | 8/1998 | Erskine |
| 5,840,024 A | 11/1998 | Taniguchi et al. |
| 5,968,082 A | 10/1999 | Heil |
| 5,984,918 A | 11/1999 | Garito et al. |
| 6,050,976 A | 4/2000 | Thorne et al. |
| 6,090,052 A | 7/2000 | Akerfeldt et al. |
| 6,102,044 A | 8/2000 | Naidyhorski |
| 6,132,368 A | 10/2000 | Cooper |
| 6,140,722 A | 10/2000 | Ballard et al. |
| 6,162,101 A | 12/2000 | Fischer et al. |
| 6,319,015 B1 | 11/2001 | Faunce |
| 6,324,416 B1 | 11/2001 | Seibert |
| 6,330,480 B1 | 12/2001 | Van der Linden et al. |
| 6,350,160 B1 | 2/2002 | Feuersanger et al. |
| 6,415,168 B1 | 7/2002 | Putz |
| 6,428,336 B1 | 8/2002 | Akerfeldt |
| 6,546,270 B1 | 4/2003 | Goldin et al. |
| 6,620,136 B1 | 9/2003 | Pressly, Sr. et al. |
| 6,663,570 B2 | 12/2003 | Mott et al. |
| 6,673,078 B1 | 1/2004 | Muncie |
| 6,714,809 B2 | 3/2004 | Lee et al. |
| 6,780,065 B2 | 8/2004 | Schwarz |
| 6,799,991 B2 | 10/2004 | Williams et al. |
| 6,913,478 B2 | 7/2005 | Lamirey |
| 7,130,699 B2 | 10/2006 | Huff et al. |
| 7,144,378 B2 | 12/2006 | Arnott |
| 7,255,609 B1 | 8/2007 | Epstein |
| 7,274,956 B2 | 9/2007 | Mott et al. |
| 7,402,083 B2 | 7/2008 | Kast et al. |
| 7,452,360 B2 | 11/2008 | Trudeau et al. |
| 7,553,193 B2 | 6/2009 | Kast et al. |
| 7,585,118 B1 | 9/2009 | Lumpkin |
| 7,633,023 B2 | 12/2009 | Cappa et al. |
| 7,666,191 B2 | 2/2010 | Orban, III et al. |
| 7,753,696 B2 | 7/2010 | Hoecke et al. |
| 7,771,394 B2 | 8/2010 | Shue et al. |
| 7,819,844 B2 | 10/2010 | Spenser et al. |
| 7,972,282 B2 | 7/2011 | Clark et al. |
| 8,105,338 B2 | 1/2012 | Anderson et al. |
| 8,147,275 B1 | 4/2012 | Drake et al. |
| 8,206,175 B2 | 6/2012 | Boyd et al. |
| 8,267,873 B2 | 9/2012 | Yanuma |
| 8,388,541 B2 | 3/2013 | Messerly et al. |
| 8,480,427 B2 | 7/2013 | Marshalok |
| 8,548,601 B2 | 10/2013 | Chinn et al. |
| 8,597,042 B2 | 12/2013 | King |
| 8,603,011 B2 | 12/2013 | Landowski |
| 8,620,412 B2 | 12/2013 | Griffiths et al. |
| 8,639,340 B2 | 1/2014 | Sommer et al. |
| 8,666,510 B2 | 3/2014 | Chinn et al. |
| 8,781,555 B2 | 7/2014 | Burnside et al. |
| 8,849,382 B2 | 9/2014 | Cox et al. |
| 8,869,887 B2 | 10/2014 | Deere et al. |
| 8,932,258 B2 | 1/2015 | Blanchard et al. |
| 8,958,878 B2 | 2/2015 | Cejnar |
| 9,059,548 B2 | 6/2015 | Stump et al. |
| 9,095,680 B2 | 8/2015 | Steegers et al. |
| 9,101,775 B2 | 8/2015 | Barker |
| 9,107,594 B2 | 8/2015 | Selvitelli et al. |
| 9,108,027 B2 | 8/2015 | Eubanks et al. |
| 9,131,956 B2 | 9/2015 | Shaughnessy et al. |
| 9,144,395 B2 | 9/2015 | Sela et al. |
| 9,425,537 B2 | 8/2016 | Barker |
| 9,456,766 B2 | 10/2016 | Cox et al. |
| 9,492,097 B2 | 11/2016 | Wilkes et al. |
| 9,521,961 B2 | 12/2016 | Silverstein et al. |
| 9,526,440 B2 | 12/2016 | Burnside et al. |
| 9,549,685 B2 | 1/2017 | Cox et al. |

(56) References Cited

U.S. PATENT DOCUMENTS

| | | |
|---|---|---|
| 9,554,716 B2 | 1/2017 | Burnside et al. |
| 9,636,031 B2 | 5/2017 | Cox |
| 9,649,048 B2 | 5/2017 | Cox et al. |
| 9,656,093 B2 | 5/2017 | Villarta et al. |
| 9,662,506 B2 | 5/2017 | Govea |
| 9,675,784 B2 | 6/2017 | Belson |
| 9,681,823 B2 | 6/2017 | Messerly et al. |
| 9,808,647 B2 | 11/2017 | Rhodes et al. |
| 9,872,971 B2 | 1/2018 | Blanchard |
| 9,919,145 B2 | 3/2018 | Bondhus et al. |
| 9,950,139 B2 | 4/2018 | Blanchard et al. |
| 9,999,371 B2 | 6/2018 | Messerly et al. |
| 10,105,121 B2 | 10/2018 | Burnside et al. |
| 10,130,806 B2 | 11/2018 | Leven et al. |
| 10,165,962 B2 | 1/2019 | Messerly et al. |
| 10,201,713 B2 | 2/2019 | Leven |
| 10,231,753 B2 | 3/2019 | Burnside et al. |
| 10,238,418 B2 | 3/2019 | Cox et al. |
| 10,238,880 B2 | 3/2019 | Thom et al. |
| 10,307,602 B2 | 6/2019 | Leven |
| 10,322,253 B2 | 6/2019 | Einav et al. |
| 10,342,575 B2 | 7/2019 | Cox et al. |
| 10,449,330 B2 | 10/2019 | Newman et al. |
| 10,524,691 B2 | 1/2020 | Newman et al. |
| 10,602,958 B2 | 3/2020 | Silverstein et al. |
| 10,751,509 B2 | 8/2020 | Misener |
| 10,772,696 B2 | 9/2020 | Thompson et al. |
| 10,992,078 B2 | 4/2021 | Thompson et al. |
| D921,884 S | 6/2021 | Tran et al. |
| 11,936,132 B2 * | 3/2024 | Thompson ......... H01R 13/7175 |
| 2002/0197905 A1 | 12/2002 | Kaufmann et al. |
| 2003/0199827 A1 | 10/2003 | Thorne |
| 2003/0216723 A1 | 11/2003 | Shinmura et al. |
| 2004/0039372 A1 | 2/2004 | Carmody |
| 2004/0146252 A1 | 7/2004 | Healy et al. |
| 2005/0177199 A1 | 8/2005 | Hansen et al. |
| 2005/0283216 A1 | 12/2005 | Pyles |
| 2006/0025677 A1 | 2/2006 | Verard et al. |
| 2006/0030864 A1 | 2/2006 | Kennedy, et al. |
| 2006/0161138 A1 | 7/2006 | Orban et al. |
| 2006/0173407 A1 | 8/2006 | Shaughnessy et al. |
| 2007/0062544 A1 | 3/2007 | Rauk Bergstrom et al. |
| 2007/0118079 A1 | 5/2007 | Moberg et al. |
| 2007/0160327 A1 | 7/2007 | Lewallen et al. |
| 2007/0161969 A1 | 7/2007 | Andersen |
| 2007/0293719 A1 | 12/2007 | Scopton et al. |
| 2008/0009720 A1 | 1/2008 | Schefelker et al. |
| 2008/0046062 A1 | 2/2008 | Camps et al. |
| 2008/0236598 A1 | 10/2008 | Gobel |
| 2008/0287876 A1 | 11/2008 | Shue et al. |
| 2008/0304793 A1 | 12/2008 | Benaron et al. |
| 2009/0156926 A1 | 6/2009 | Messerly et al. |
| 2009/0234328 A1 | 9/2009 | Cox et al. |
| 2010/0036227 A1 | 2/2010 | Cox et al. |
| 2010/0049126 A1 | 2/2010 | Bronfeld et al. |
| 2010/0139669 A1 | 6/2010 | Piferi et al. |
| 2010/0204569 A1 | 8/2010 | Burnside et al. |
| 2011/0015533 A1 | 1/2011 | Cox et al. |
| 2011/0160824 A1 | 6/2011 | Ware et al. |
| 2011/0166528 A1 | 7/2011 | Millerd et al. |
| 2011/0250775 A1 | 10/2011 | Bies et al. |
| 2011/0257503 A1 | 10/2011 | Mehdizadeh et al. |
| 2011/0282188 A1 | 11/2011 | Burnside et al. |
| 2011/0295108 A1 | 12/2011 | Cox et al. |
| 2012/0071752 A1 | 3/2012 | Sewell et al. |
| 2012/0143029 A1 | 6/2012 | Silverstein et al. |
| 2012/0220854 A1 | 8/2012 | Messerly et al. |
| 2012/0253320 A1 | 10/2012 | Steegers et al. |
| 2013/0006102 A1 | 1/2013 | Wilkes et al. |
| 2013/0023729 A1 | 1/2013 | Vazales et al. |
| 2013/0060116 A1 | 3/2013 | Messerly et al. |
| 2013/0095689 A1 | 4/2013 | Hayman et al. |
| 2013/0104884 A1 | 5/2013 | Vazales et al. |
| 2013/0109980 A1 | 5/2013 | Teo |
| 2013/0211225 A1 | 8/2013 | Zhang |
| 2013/0245434 A1 | 9/2013 | Messerly et al. |
| 2013/0247921 A1 | 9/2013 | Dye et al. |
| 2013/0289417 A1 | 10/2013 | Grunwald et al. |
| 2013/0308137 A1 | 11/2013 | Manzke et al. |
| 2013/0331688 A1 | 12/2013 | Heigl et al. |
| 2013/0337674 A1 | 12/2013 | Stump et al. |
| 2014/0031674 A1 | 1/2014 | Newman et al. |
| 2014/0046261 A1 | 2/2014 | Newman et al. |
| 2014/0107475 A1 | 4/2014 | Cox et al. |
| 2014/0150782 A1 | 6/2014 | Vazales et al. |
| 2014/0188133 A1 | 7/2014 | Misener |
| 2014/0303492 A1 | 10/2014 | Burnside et al. |
| 2015/0012072 A1 | 1/2015 | Johnson et al. |
| 2015/0018701 A1 | 1/2015 | Cox et al. |
| 2015/0031987 A1 | 1/2015 | Pameijer et al. |
| 2015/0105654 A1 | 4/2015 | Meyer |
| 2015/0148615 A1 | 5/2015 | Brennan et al. |
| 2015/0164583 A1 | 6/2015 | Zarins et al. |
| 2015/0177467 A1 | 6/2015 | Gniadek et al. |
| 2015/0190615 A1 | 7/2015 | Shaltis |
| 2015/0223897 A1 | 8/2015 | Kostrzewski et al. |
| 2015/0297114 A1 | 10/2015 | Cox et al. |
| 2015/0305816 A1 | 10/2015 | Hadzic |
| 2016/0018602 A1 | 1/2016 | Govari et al. |
| 2016/0213432 A1 | 7/2016 | Flexman et al. |
| 2017/0014194 A1 | 1/2017 | Duindam et al. |
| 2017/0020561 A1 | 1/2017 | Cox et al. |
| 2017/0079548 A1 | 3/2017 | Silverstein et al. |
| 2017/0079615 A1 | 3/2017 | Burnside et al. |
| 2017/0079681 A1 | 3/2017 | Burnside et al. |
| 2017/0181646 A1 | 6/2017 | Hayes et al. |
| 2017/0231700 A1 | 8/2017 | Cox et al. |
| 2017/0261699 A1 | 9/2017 | Compton et al. |
| 2017/0281029 A1 | 10/2017 | Messerly et al. |
| 2017/0333136 A1 | 11/2017 | Hladio et al. |
| 2018/0071509 A1 | 3/2018 | Tran et al. |
| 2018/0110951 A2 | 4/2018 | Beard |
| 2018/0116551 A1 | 5/2018 | Newman et al. |
| 2018/0140170 A1 | 5/2018 | Van Putten et al. |
| 2018/0289927 A1 | 10/2018 | Messerly |
| 2018/0296122 A1 | 10/2018 | Messerly et al. |
| 2019/0069877 A1 | 3/2019 | Burnside et al. |
| 2019/0099108 A1 | 4/2019 | Messerly et al. |
| 2019/0180647 A1 | 6/2019 | Fujiki |
| 2019/0231172 A1 | 8/2019 | Barron et al. |
| 2019/0237902 A1 | 8/2019 | Thompson et al. |
| 2019/0350621 A1 | 11/2019 | Zitnick et al. |
| 2019/0350663 A1 | 11/2019 | Thompson et al. |
| 2020/0054858 A1 | 2/2020 | Newman et al. |
| 2020/0138332 A1 | 5/2020 | Newman et al. |
| 2020/0221934 A1 | 7/2020 | Van Der Mark et al. |
| 2020/0237255 A1 | 7/2020 | Silverstein et al. |
| 2020/0345441 A1 | 11/2020 | Thompson et al. |
| 2021/0030504 A1 | 2/2021 | Thompson et al. |
| 2021/0038322 A1 | 2/2021 | Thompson et al. |
| 2022/0110707 A1 | 4/2022 | Sowards et al. |
| 2022/0110708 A1 | 4/2022 | Misener et al. |
| 2022/0128770 A1 | 4/2022 | Sowards et al. |
| 2022/0241044 A1 | 8/2022 | Thompson et al. |
| 2023/0248459 A1 | 8/2023 | Thompson et al. |
| 2023/0390015 A1 | 12/2023 | Thompson et al. |

FOREIGN PATENT DOCUMENTS

| | | |
|---|---|---|
| EP | 3673801 A1 | 7/2020 |
| WO | 9413201 | 6/1994 |
| WO | 9619017 | 6/1996 |
| WO | 9822180 A1 | 5/1998 |
| WO | 2004101068 A1 | 11/2004 |
| WO | 2005016451 A1 | 2/2005 |
| WO | 2005044332 A2 | 5/2005 |
| WO | 2005072807 A1 | 8/2005 |
| WO | 2005077453 A2 | 8/2005 |
| WO | 2007058816 A2 | 5/2007 |
| WO | 2007109285 A2 | 9/2007 |
| WO | 2007149618 A2 | 12/2007 |
| WO | 2009050599 A2 | 4/2009 |
| WO | 2010123701 A1 | 10/2010 |
| WO | 2011033107 A1 | 3/2011 |

(56) References Cited

FOREIGN PATENT DOCUMENTS

| WO | 2011082160 A2 | 7/2011 |
|---|---|---|
| WO | 2012102745 A2 | 8/2012 |
| WO | 2015075002 A1 | 5/2015 |
| WO | 2016146993 A1 | 9/2016 |
| WO | 2019148201 A1 | 8/2019 |
| WO | 2019165011 A1 | 8/2019 |
| WO | 2019221926 A1 | 11/2019 |
| WO | 2021021408 A1 | 2/2021 |
| WO | 2021026502 A1 | 2/2021 |
| WO | 2022081583 A1 | 4/2022 |
| WO | 2022081591 A1 | 4/2022 |
| WO | 2022093991 A1 | 5/2022 |

OTHER PUBLICATIONS

EP 20849119.1 filed Mar. 4, 2022 Extended European Search Report dated Jun. 26, 2023.
PCT/US19/30470 filed May 2, 2019 International Search Report and Written Opinion dated Jul. 19, 2019.
PCT/US2019/015710 filed Jan. 29, 2019 International Preliminary Report on Patentability dated Apr. 29, 2019.
PCT/US2019/015710 filed Jan. 29, 2019 International Search Report and Written Opinion dated Apr. 29, 2019.
PCT/US2019/018851 filed Feb. 20, 2019 Internation Search Report and Written Opinion dated May 7, 2019.
PCT/US2019/018851 filed Feb. 20, 2019 International Preliminary Report on Patentability dated May 7, 2019.
PCT/US2020/41267 filed Jul. 8, 2020 Internation Search Report and Written Opinion dated Oct. 1, 2020.
PCT/US2020/45498 filed Aug. 7, 2020 International Search Report and Written Opinion dated Oct. 4, 2020.
PCT/US2021/054593 filed Oct. 12, 2021 International Search Report and Written Opinion dated Jan. 24, 2022.
PCT/US2021/054607 filed Oct. 12, 2021 International Search Report and Written Opinion dated Jan. 21, 2022.
PCT/US2021/056896 filed Oct. 27, 2021 International Search Report and Written Opinion dated Mar. 22, 2022.
U.S. Appl. No. 12/426,175, filed Apr. 17, 2009 Advisory Action dated Nov. 26, 2013.
U.S. Appl. No. 12/426,175, filed Apr. 17, 2009 Decision on Appeal dated Nov. 7, 2016.
U.S. Appl. No. 12/426,175, filed Apr. 17, 2009 Examiner's Answer dated Oct. 7, 2014.
U.S. Appl. No. 12/426,175, filed Apr. 17, 2009 Final Office Action dated Aug. 2, 2013.
U.S. Appl. No. 12/426,175, filed Apr. 17, 2009 Final Office Action dated Jan. 31, 2014.
U.S. Appl. No. 12/426,175, filed Apr. 17, 2009 Non-Final Office Action dated Dec. 3, 2012.
U.S. Appl. No. 12/426,175, filed Apr. 17, 2009 Notice of Allowance dated Dec. 13, 2016.
U.S. Appl. No. 12/715,556, filed Mar. 2, 2010 Final Office Action dated Oct. 2, 2013.
U.S. Appl. No. 12/715,556, filed Mar. 2, 2010 Non-Final Office Action dated Sep. 13, 2012.
U.S. Appl. No. 15/585,051, filed May 2, 2017 Examiner's Answer dated May 2, 2019.
U.S. Appl. No. 15/585,051, filed May 2, 2017 Final Office Action dated Feb. 28, 2018.
U.S. Appl. No. 15/585,051, filed May 2, 2017 Final Office Action dated Mar. 15, 2018.
U.S. Appl. No. 15/585,051, filed May 2, 2017 Non-Final Office Action dated Jul. 14, 2017.
U.S. Appl. No. 16/261,368, filed Jan. 29, 2019 Advisory Action dated Jul. 21, 2020.
U.S. Appl. No. 16/261,368, filed Jan. 29, 2019 Non-Final Office Action dated Jan. 23, 2020.
U.S. Appl. No. 16/261,368, filed Jan. 29, 2019 Notice of Allowance dated Jan. 15, 2021.
U.S. Appl. No. 16/281,079, filed Feb. 20, 2019 Board Decision dated Jun. 6, 2023.
U.S. Appl. No. 16/281,079, filed Feb. 20, 2019 Examiner's Answer dated Feb. 25, 2022.
U.S. Appl. No. 16/281,079, filed Feb. 20, 2019 Final Office Action dated Aug. 25, 2020.
U.S. Appl. No. 16/281,079, filed Feb. 20, 2019 Non-Final Office Action dated Apr. 1, 2020.
U.S. Appl. No. 16/281,079, filed Feb. 20, 2019 Non-Final Office Action dated Apr. 20, 2021.
U.S. Appl. No. 16/402,074, filed May 2, 2019 Non-Final Office Action dated Apr. 16, 2020.
U.S. Appl. No. 16/923,912, filed Jul. 8, 2020 Notice of Allowance dated Mar. 27, 2023.
U.S. Appl. No. 16/932,425, filed Jul. 17, 2020 Non-Final Office Action dated Jun. 18, 2021.
U.S. Appl. No. 16/932,425, filed Jul. 17, 2020 Notice of Allowance dated Jan. 10, 2022.
U.S. Appl. No. 16/988,452, filed Aug. 7, 2020 Advisory Action dated Oct. 2, 2023.
U.S. Appl. No. 16/988,452, filed Aug. 7, 2020 Final Office Action dated Mar. 16, 2023.
U.S. Appl. No. 16/988,452, filed Aug. 7, 2020 Non-Final Office Action dated Mar. 16, 2023.
U.S. Appl. No. 16/988,452, filed Aug. 7, 2020 Non-Final Office Action dated Nov. 9, 2023.
U.S. Appl. No. 17/240,826, filed Apr. 26, 2021 Notice of Allowance dated Nov. 9, 2023.
U.S. Appl. No. 17/240,826, filed Apr. 26, 2021, Non-Final Office Action dated Jul. 19, 2023.
U.S. Appl. No. 17/512,501, filed Oct. 27, 2021 Final Office Action dated Aug. 31, 2023.
U.S. Appl. No. 17/512,501, filed Oct. 27, 2021 Non-Final Office Action dated Feb. 17, 2023.
U.S. Appl. No. 17/512,501, filed Oct. 27, 2021 Restriction Requirement dated Sep. 30, 2022.
U.S. Appl. No. 17/723,246, filed Apr. 18, 2022, Non-Final Office Action dated Sep. 27, 2022.
U.S. Appl. No. 17/723,246, filed Apr. 18, 2022, Notice of Allowance dated Jan. 27, 2023.
U.S. Appl. No. 18/135,330, filed Apr. 17, 2023, Non-Final Office Action dated Dec. 18, 2023.
U.S. Appl. No. 29/658,136 Specification and Drawings filed Jul. 27, 2018.
U.S. Appl. No. 16/988,452, filed Aug. 7, 2020 Notice of Allowance dated Feb. 29, 2024.
U.S. Appl. No. 17/499,635, filed Oct. 12, 2021 Restriction Requirement dated Jun. 12, 2024.
U.S. Appl. No. 17/512,501, filed Oct. 27, 2021 Examiner's Answer dated Jun. 18, 2024.
U.S. Appl. No. 18/135,330, filed Apr. 17, 2023, Non-Final Office Action dated Jul. 15, 2024.
U.S. Appl. No. 18/235,334, filed Aug. 17, 2023, Notice of Allowance dated Apr. 4, 2024.

* cited by examiner

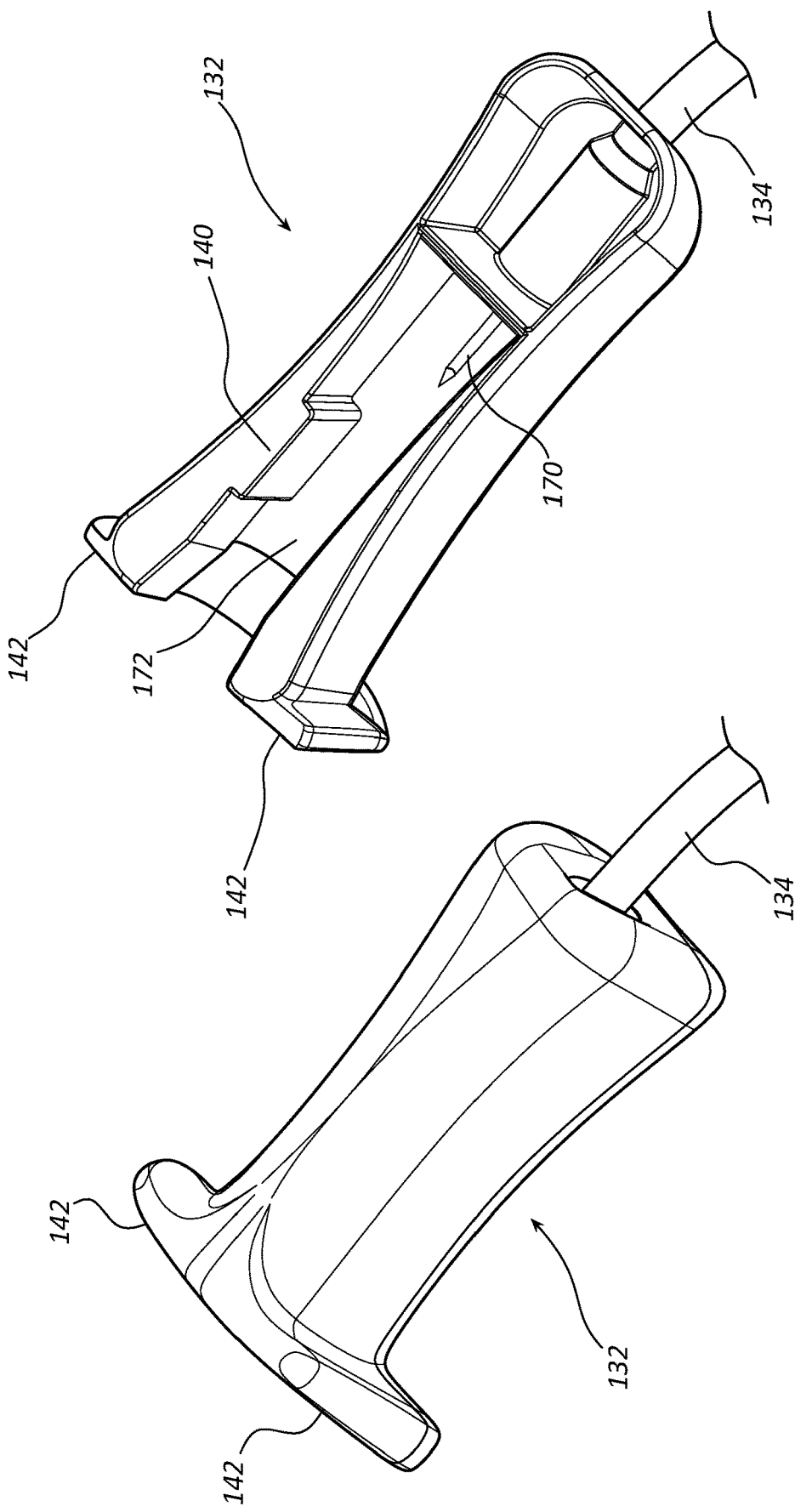

CONNECTION SYSTEM FOR ESTABLISHING AN ELECTRICAL CONNECTION THROUGH A DRAPE AND METHODS THEREOF

PRIORITY

This application is a continuation of U.S. patent application Ser. No. 17/240,826, filed Apr. 26, 2021, now U.S. Pat. No. 11,936,132, which is a continuation of U.S. patent application Ser. No. 16/261,368, filed Jan. 29, 2019, now U.S. Pat. No. 10,992,078, which claims the benefit of priority to U.S. Provisional Application No. 62/623,394, filed Jan. 29, 2018, each of which is incorporated by reference in its entirety into this application.

BACKGROUND

In a typical surgical procedure, a sterile drape is placed over a patient to establish a sterile field, within which the surgical procedure is performed. For example, in a typical catheter-placement procedure, a sterile drape is placed over a patient to establish a sterile field for placement of the catheter. However, there is often a need to breach the sterile barrier in order to make electrical connections between components of various systems without compromising the sterility of the sterile field. Disclosed herein is a connection system for establishing an electrical connection through a drape and methods thereof that address at least the foregoing need.

SUMMARY

Disclosed herein is a connection system including, in some embodiments, a first connector and a second connector configured for establishing one or more electrical connections through a drape. The first connector includes an alignment protrusion and a first piercing element configured to pierce the drape. The first piercing element has one or more electrical contacts. The second connector includes an alignment notch, a channel, and a first receptacle configured to receive the first piercing element when inserted therein. The alignment notch is configured to accept the alignment protrusion when the first connector is aligned with the second connector then inserted into the second connector. The channel, which is along a length of the second connector, is configured to allow the alignment protrusion to slide along the channel. The first receptacle has one or more electrical contacts configured to form at least a first electrical connection of the one or more electrical connections with the first connector when the first piercing element is inserted in the first receptacle.

In some embodiments, the first piercing element is a jack plug and the first receptacle is a jack. The jack plug has a needle-like tip electrical contact, one or more ring electrical contacts, and a sleeve electrical contact. The jack has complementary electrical contacts.

In some embodiments, the first piercing element is a blade-like end portion of a printed circuit board having the one or more electrical contacts thereon, and the first receptacle is a slot having complementary electrical contacts.

In some embodiments, the connection system further includes a seal configured as a sticker disposed within the first connector around a proximal-end portion of the piercing element. The sticker is configured to adhere to the drape about a piercing thereof. The sticker is configured to selectively pull away from the first connector when the first connector and the second connector are disconnected, thereby sealing the drape.

In some embodiments, the seal is a self-sealing polymer septum.

In some embodiments, the connection system further includes a second piercing element of the first connector and a second receptacle of the second connector, each of which includes one or more electrical contacts. The second piercing element is configured to pierce the drape in a location different than the first piercing element. The second receptacle is configured to form at least a second electrical connection of the one or more electrical connections when the second piercing element is inserted in the second receptacle.

In some embodiments, the connection system further includes a third piercing element of the first connector and a third receptacle of the second connector, each of which includes one or more electrical contacts. The third piercing element is configured to pierce the drape in a location different than the first and second piercing elements. The third receptacle is configured to form at least a third electrical connection of the one or more electrical connections when the third piercing element is inserted in the third receptacle.

In some embodiments, the connection system further includes a seal configured as a sticker disposed within the first connector around proximal-end portions of the piercing elements. The sticker is configured to adhere to the drape about piercings thereof. The sticker is configured to selectively pull away from the first connector when the first connector and the second connector are disconnected, thereby sealing the drape.

In some embodiments, the seal is a self-sealing polymer septum.

In some embodiments, the connection system further includes a light-emitting diode ("LED") on the first connector configured to change from a first state to a second state to indicate success in forming the one or more electrical connections.

In some embodiments, the LED is configured to change from the first state to the second state upon completion of a dedicated LED circuit when forming the one or more electrical connections.

In some embodiments, the first connector includes a pair of finger pads about a distal-end portion of the first connector configured for pushing or pulling the first connector along the channel of the second connector.

In some embodiments, the alignment protrusion of the first connector and the alignment notch and channel of the second connector are parts of a one-handed mechanism by which the first connector and the second connector are connected to form the one or more electrical connections. The one-handed mechanism is configured to tighten the drape between the first connector and the second connector without bunching the drape.

In some embodiments, the first connector is transparent, which allows a connection between the first connector and the second connector by way of the one-handed mechanism to be viewed.

Also disclosed herein is a connection system including, in some embodiments, a tether connector and a fin connector configured for establishing one or more electrical connections through a drape. The tether connector is coupled to a stylet configured to be removably disposed in a catheter. The tether connector includes a pair of alignment protrusions and a piercing element configured to pierce the drape from a sterile side of the drape. The pair of alignment protrusions are within a distal-end portion of the tether connector. The piercing element has one or more electrical contacts. The fin connector is part of a tip-location sensor configured to sense a location of a tip of the catheter in a patient. The fin connector has a pair of alignment notches, a pair of channels, and a receptacle configured to receive the piercing element when inserted therein. The pair of alignment notches are in a medial portion of the fin connector. The pair of alignment notches are configured to accept the pair of alignment protrusions when the tether connector is aligned with the fin connector then inserted into the fin connector. The pair of channels, which are along a length of the fin connector, are configured to allow the pair of alignment protrusions to slide along the pair of channels with the drape between the pair of alignment protrusions and the pair of channels. The pair of alignment protrusions of the tether connector and the pair of alignment notches and channels are parts of a one-handed drape-tightening mechanism by which the tether connector and the fin connector are connected to form the one or more electrical connections. The receptacle has one or more electrical contacts configured to form one or more electrical connections with the one or more electrical contacts of the tether connector when the piercing element is inserted in the receptacle.

In some embodiments, the piercing element is a jack plug and the receptacle is a jack. The jack plug has a needle-like tip electrical contact, one or more ring electrical contacts, and a sleeve electrical contact. The jack has complementary electrical contacts.

In some embodiments, the piercing element is a blade-like end portion of a printed circuit board having the one or more electrical contacts thereon, and the receptacle is a slot having complementary electrical contacts.

In some embodiments, the connection system further includes a self-sealing polymer septum configured as a sticker disposed within the tether connector around a proximal-end portion of the piercing element. The sticker is configured to adhere to the drape about a piercing thereof. The sticker is configured to selectively pull away from the tether connector when the tether connector and the fin connector are disconnected, thereby sealing the drape.

In some embodiments, the connection system further includes an LED on the tether connector and a dedicated LED circuit. The LED is configured to change from a first state to a second state upon completion of the dedicated LED circuit when forming the one or more electrical connections, thereby indicating success in forming the one or more electrical connections.

In some embodiments, the tether connector includes a pair of finger pads about a distal-end portion of the tether connector configured for pushing or pulling the tether connector along the pair of channels of the fin connector.

Also disclosed herein is a method including, in some embodiments, establishing one or more electrical connections through a drape by placing the drape over a second connector of a connection system; aligning a pair of alignment protrusions within a distal-end portion of a first connector of the connection system with a pair of alignment notches in a medial portion of the second connector; disposing the first connector over the second connector with the drape between the first connector and the second connector, the drape self-tightening over the second connector while disposing the first connector over the second connector; sliding the pair of alignment protrusions of the first connector along a pair of channels along a length of the second connector with the drape between the pair of alignment protrusions and the pair of channels; piercing a sterile side of the drape with a piercing element of the first connector, the piercing element having one or more electrical contacts; inserting the piercing element into a receptacle of the second connector, the receptacle having one or more electrical contacts; and forming the one or more electrical connections respectively between the one or more electrical contacts of the piercing element and the one or more electrical contacts of the receptacle.

In some embodiments, the first connector includes a pair of finger pads about the distal-end portion of the first connector configured for pushing or pulling the first connector with one hand when sliding the first connector along the second connector.

In some embodiments, the method further includes viewing the disposing of the first connector over the second connector and the sliding of the first connector along the second connector through the first connecter, wherein the first connector is transparent.

In some embodiments, the piercing element is a jack plug and the receptacle is a jack. The jack plug has a needle-like tip electrical contact, one or more ring electrical contacts, and a sleeve electrical contact. The jack has complementary electrical contacts.

In some embodiments, the piercing element is a blade-like end portion of a printed circuit board having the one or more electrical contacts thereon, and the receptacle is a slot having complementary electrical contacts.

In some embodiments, the method further includes sealing the drape with a self-sealing polymer septum disposed within the first connector around a proximal-end portion of the piercing element. The septum is configured as a sticker to adhere to the drape about a piercing thereof.

In some embodiments, the method further includes confirming success in forming the one or more electrical connections by a change from a first state of an LED on the first connector to a second state of the LED upon forming the one or more electrical connections.

In some embodiments, the first connector is a tether connector coupled to a stylet configured to be removably disposed in a catheter, and the second connector is fin connector of a tip-location sensor configured to sense a location of a tip of the catheter in a patient.

These and other features of the concepts provided herein will become more apparent to those of skill in the art in view of the accompanying drawings and following description, which disclose particular embodiments of such concepts in greater detail.

BRIEF DESCRIPTION OF DRAWINGS

FIG. 5A illustrates a top side of a first connector of a connection system in accordance with some embodiments.

FIG. 5B illustrates a bottom side of the first connector of the connection system in accordance with some embodiments.

DESCRIPTION

Figure 1:
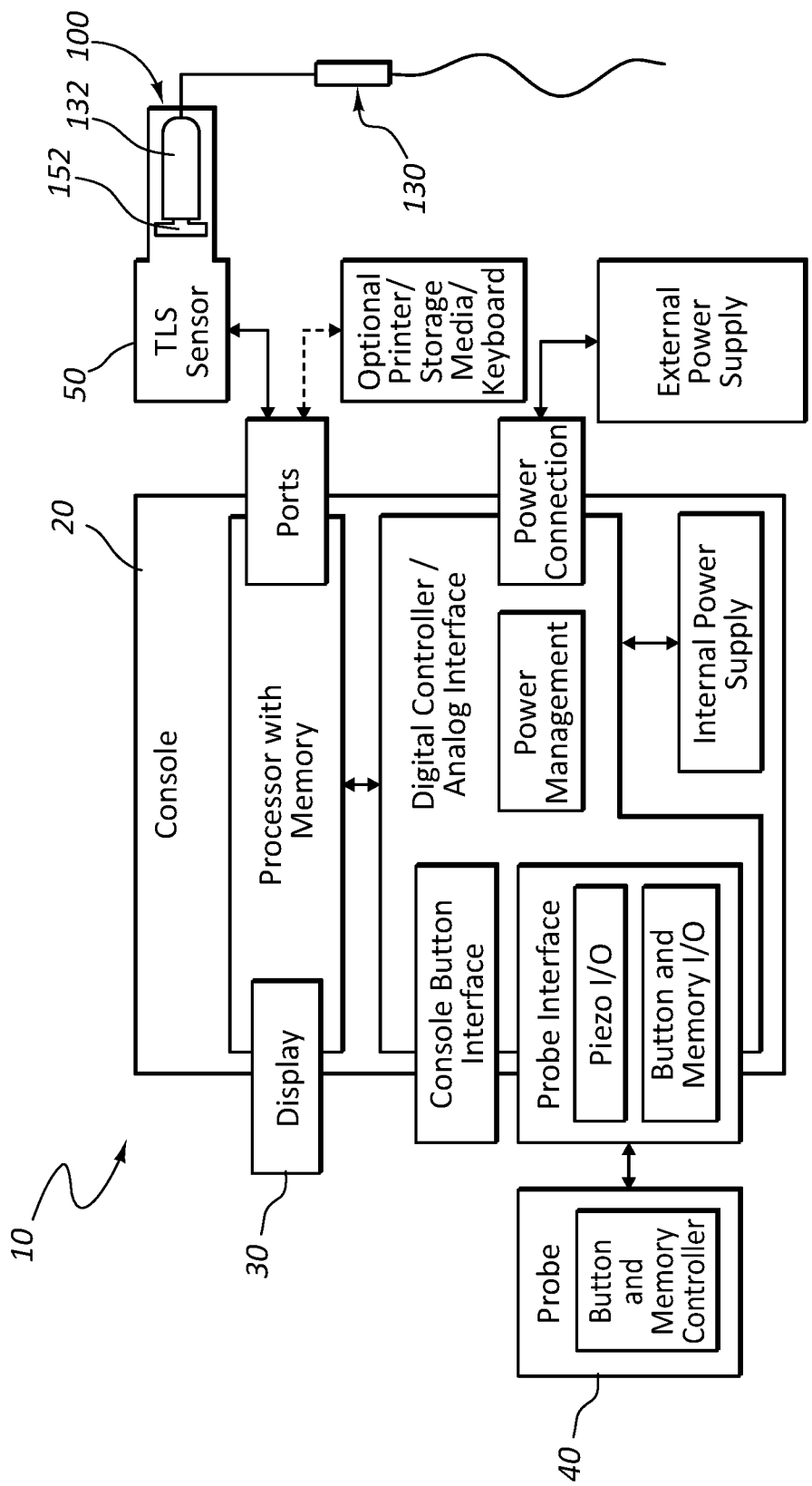
FIG. 1 illustrates a block diagram of a catheter-placement system for placing a catheter in a patient's body in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

In a typical surgical procedure, a sterile drape is placed over a patient to establish a sterile field, within which the surgical procedure is performed. For example, in a typical catheter-placement procedure, a sterile drape is placed over a patient to establish a sterile field for placement of the catheter. However, there is often a need to breach the sterile barrier in order to make electrical connections between components of various systems without compromising the sterility of the sterile field. Disclosed herein is a connection system for establishing an electrical connection through a drape and methods thereof that address at least the foregoing need.

For example, a connection system is disclosed including a first connector and a second connector configured for establishing one or more electrical connections through a drape. The first connector includes an alignment protrusion and a first piercing element configured to pierce the drape. The first piercing element has one or more electrical contacts. The second connector includes an alignment notch, a channel, and a first receptacle configured to receive the first piercing element when inserted therein. The alignment notch is configured to accept the alignment protrusion when the first connector is aligned with the second connector then inserted into the second connector. The channel, which is along a length of the second connector, is configured to allow the alignment protrusion to slide along the channel. The first receptacle has one or more electrical contacts configured to form at least a first electrical connection of the one or more electrical connections with the first connector when the first piercing element is inserted in the first receptacle.

An example catheter-placement system incorporating the connection system will be at least initially described to provide context for the connection system. It should be understood the connection system is not limited to the example catheter-placement system. Indeed, the connection system can be incorporated into any system of various systems having the need to breach a sterile barrier between components of the system in order to make electrical connections therebetween without compromising the sterility of the sterile field.

Figure 2:
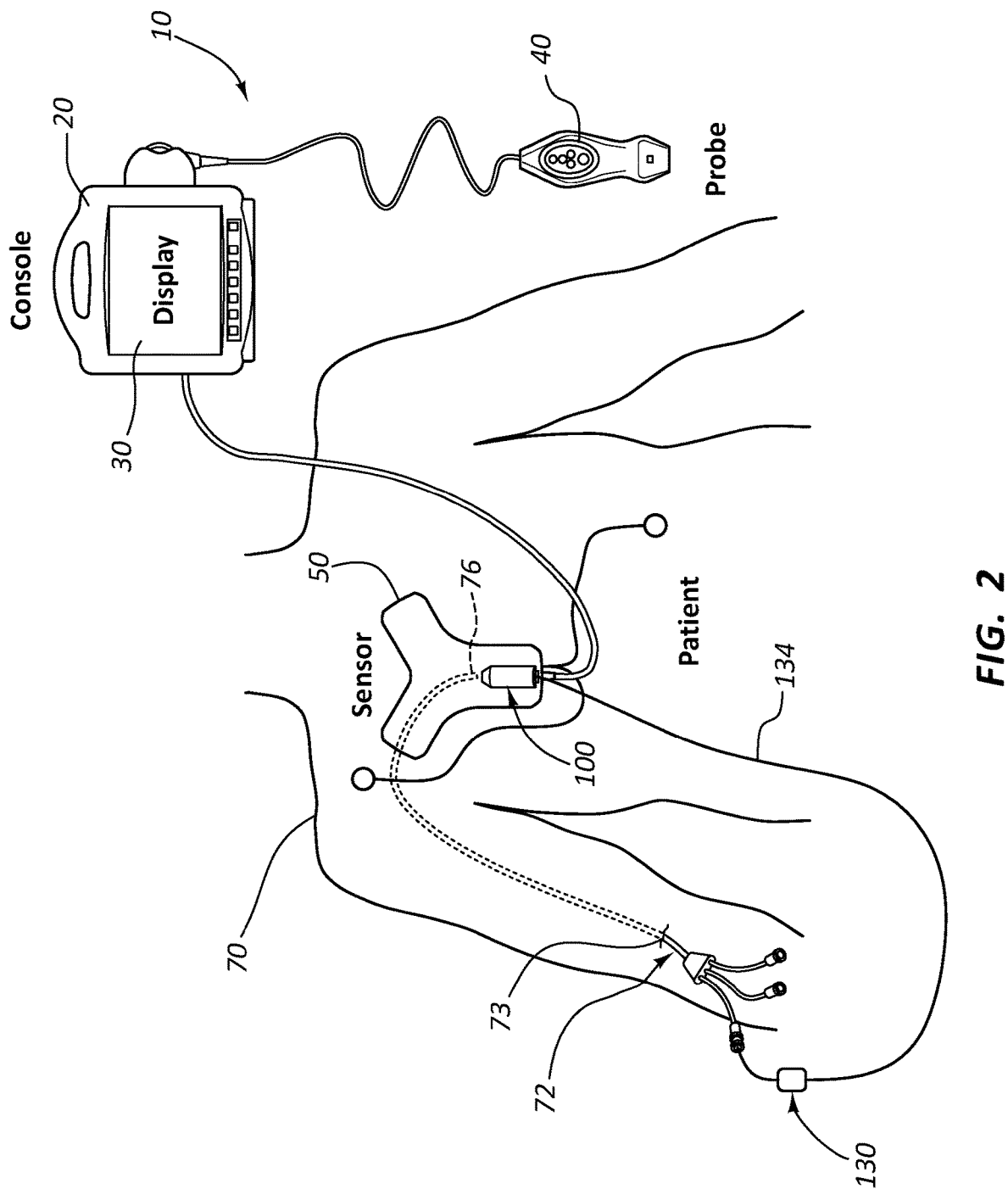
FIG. 2 illustrates the catheter-placement system and the patient in accordance with some embodiments.

FIG. 1 illustrates a block diagram of a catheter-placement system 10 for placing a catheter 72 in a body of a patient 70 in accordance with some embodiments. FIG. 2 illustrates the catheter-placement system 10 and the patient 70 in accordance with some embodiments. The catheter-placement system 10 is configured for assisting a clinician in placing the catheter 72 in a vasculature of the patient 70. As shown, the catheter-placement system 10 includes a console 20 including a display 30, an ultrasound probe 40, and a tip-location sensor 50 configured for placement on the patient's chest or some other portion of the patient's body.

Figure 3:
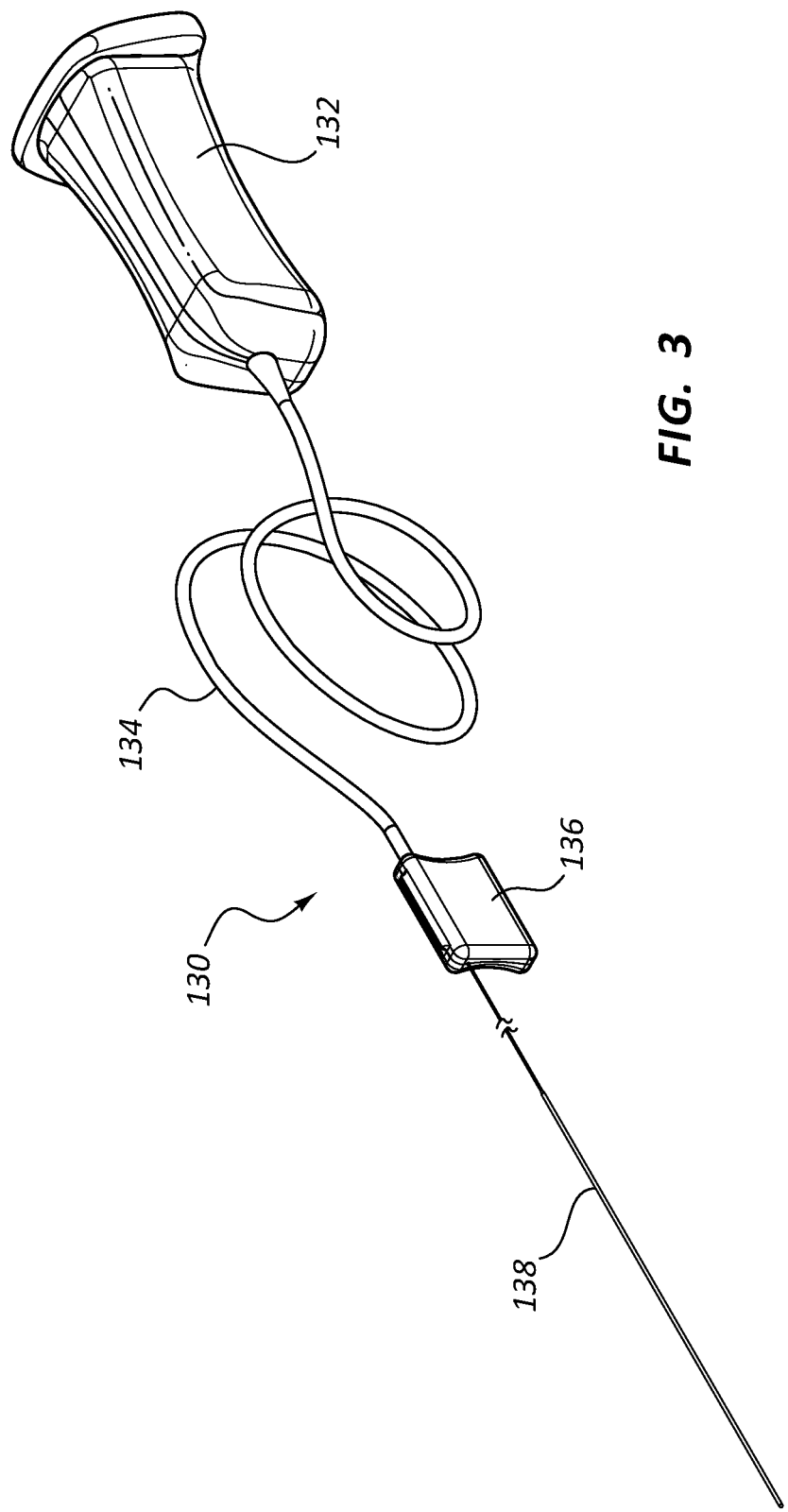
FIG. 3 illustrates a stylet including a tether connector of the catheter-placement system in accordance with some embodiments.

FIG. 3 illustrates a stylet 130 including a tether connector 132 of the catheter-placement system 10 in accordance with some embodiments. The stylet 130 is employed with the catheter 72 during insertion of the catheter 72 into the vasculature of the patient 70. The stylet 130 includes a core wire 138 configured to be removably disposed in a lumen of the catheter 72 during a catheter-placement procedure, thereby enabling a distal tip 76 of the catheter 72 to be tracked by the catheter-placement system 10 using one or more of modalities for guiding the catheter 72 to a desired location within the patient's vasculature after insertion of the catheter 72 into a percutaneous insertion site 73 of the patient 70. The one or more modalities include, but are not limited to ultrasound-based imaging of subcutaneous tissue of the patient in preparation for insertion of the catheter 72; magnet-based tracking for determining orientation, advancement direction, and general internal location of the distal tip 76 of the catheter 72; or ECG-based confirmation for confirming the distal tip 76 of the catheter 72 is positioned at a desired location. The stylet 130 further includes a tether 134 proximally extending from a handle 136, the tether 134 terminating at a proximal end thereof with a tether connector 132. The tether connector 132 is configured to mechanically couple and electrically connect with a fin connector 152 of the tip-location sensor 50 as shown in FIG. 4 in accordance with some embodiments of a connection system 100.

Additional details for the catheter-placement system 10 shown in FIGS. 1-3 can be found in U.S. Pat. No. 9,649,048, which is incorporated by reference in its entirety into this application.

Figure 4:
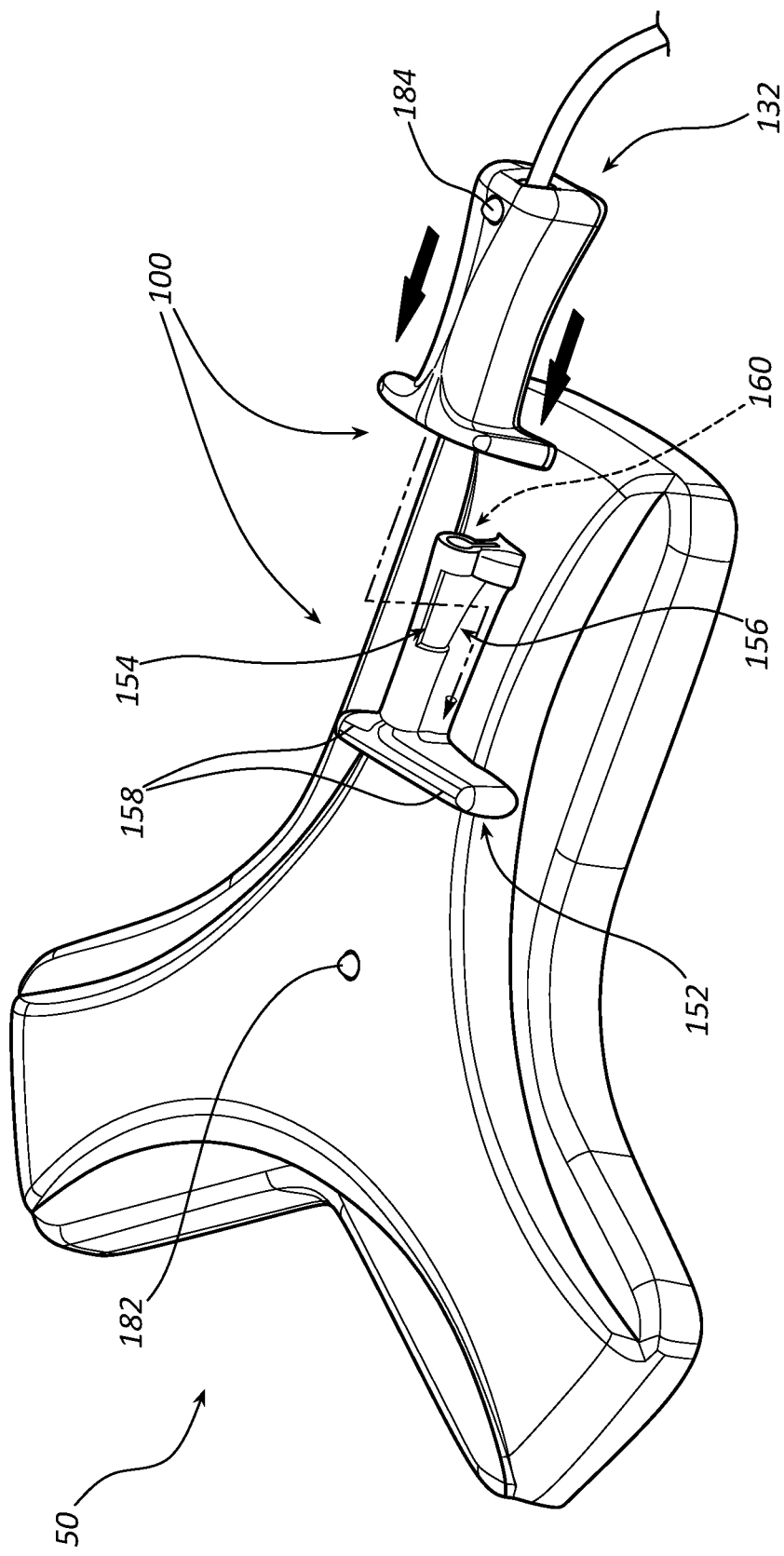
FIG. 4 illustrates a tip-location sensor including a fin connector of the catheter-placement system in accordance with some embodiments.

FIG. 4 illustrates the tip-location sensor 50 and the fin connector 152 of the catheter-placement system 10 in accordance with some embodiments. As shown, the fin connector 152 is disposed on the tip-location sensor 50 of the catheter-placement system 10. Again, the tether connector 132 is configured to mechanically couple and electrically connect with the fin connector 152, which enables the catheter-placement system 10 to track the distal tip 76 of the catheter 72. A drape including a sterile drape configured to provide a sterile field about the patient 70 can be interposed between the tip-location sensor 50 (e.g., under the sterile drape in a non-sterile field) and the stylet 130 (e.g., over the sterile drape in the sterile field). The tether connector 132 includes a piercing element 170 disposed with a channel 172 (see FIG. 5B) in a body of the tether connector 132, wherein the piercing element 170 is configured to pierce the drape and insert into a receptacle 160 of the fin connector 152 to electrically connect the tether connector 132 and the fin connector 152.

As shown in FIG. 4, the catheter-placement system 10, or the connection system 100 thereof, can include one or more LEDs configured to change from a first state to a second state to indicate success in forming one or more electrical connections between the tether connector 132 and the fin connector 152. The one or more LEDs can include an LED 182 on the tip-location sensor 50, an LED 184 on the tether connector 132, or both of the foregoing LEDs. Upon success in forming the one or more electrical connections between the tether connector 132 and the fin connector 152, each LED of the one or more LEDs can change from a first state of being off to a second state of being on, a first state of being one color (e.g., red) to a second state of being another color (e.g., green), a first state of blinking light to a second state of a solid light, or various combinations thereof. Each LED of the one or more LEDs is configured to change from the first state to the second state upon completion of a dedicated LED circuit for the change of state upon forming the one or more electrical connections. The LED 362 is configured to be bright enough to see through a drape, thus enabling a clinician to see the indicator 362 even when the drape is in place.

In view of the foregoing catheter-placement system 10, the connection system 100 includes a first connector such as the tether connector 132 and a second connector such as the fin connector 152 configured for mechanically coupling and establishing one or more electrical connections through a sterile drape without compromising the sterile field set up by the sterile drape. Having described the connection system 100 in the context of the catheter-placement system 10, additional details for the first connector and the second connector of the connection system 100 will now be described. For convenience, the first connector and the second connector of the connection system 100 will now respectively assume the reference numerals 132 and 152.

FIG. 5A illustrates a top side of the first connector 132 of the connection system 100, and FIG. 5B illustrates a bottom side of the first connector 132 of the connection system 100 in accordance with some embodiments. Reference is again made to FIG. 4, which illustrates the second connector 152 of the connection system 100 in accordance with some embodiments.

With respect to mechanically coupling the first connector and the second connector, the first connector 132 and the second connector 152 can include interlocking elements for interlocking with each other. The first connector 132 can include an alignment protrusion 140, while the second connector 152 can include an alignment notch 154 and a channel 156. The alignment notch 154 is configured to accept the alignment protrusion 140 when the alignment protrusion 140 of the first connector 132 is aligned with alignment notch 154 of the second connector 152 then inserted into the second connector 152. The channel 156, which is along a length of the second connector 152, is configured to allow the alignment protrusion 140 to slide along the channel 156. While not shown, the first connector 132 and the second connector 152 can have symmetric interlocking elements similar to the foregoing interlocking elements. For example, the first connector 132 can have a pair of alignment protrusions, while the second connector 152 can include a complementary pair of alignment notches and channels. While a drape is not show in FIG. 4, when a drape is interposed between the first connector 132 and the second connector 152, inserting the first connector 132 into the second connector 152 also draws and tightens the drape around the second connector 152, as well as secures the drape around the second connector 152 with the first connector 132. The alignment protrusion 140 of the first connector 132 and the alignment notch 154 and channel 156 of the second connector 152 are parts of a one-handed mechanism by which the first connector 132 and the second connector 152 are mechanically coupled for establishing the one or more electrical connections, which has the added benefit of tightening the drape between the first connector 132 and the second connector 152 without bunching the drape.

The one-handed mechanism for mechanically coupling the first connector 132 and the second connector 152 is facilitated by one or more additional features of the first connector 132 or the second connector 152. In an example, the first connector 132 can be transparent, which allows a connection between the first connector 132 and the second connector 152 to be viewed while the connection is being made by the one-handed mechanism. In another example, the first connector 132 can include a pair of finger pads 142 about a distal-end portion of the first connector 132. As shown, the pair of finger pads 142 is orthogonal to a longitudinal centerline of the first connector 132, thereby forming a 'T' shape with a body of the first connector 132. The pair of finger pads 142 is configured for pushing or pulling the first connector 132 along the second connector 152 with one or more fingers in accordance with the one-handed mechanism. Advantageously, the pair of finger pads 142 obviates compression of a medial portion of the first connector 132 resulting from pinching the medial portion, which compression can make it difficult to dispose the first connector 132 over the second connector 152 and subsequently slide the first connector 132 along the second connector 152.

Like the first connector 132, the second connector 152 can include a pair of tabs 158 orthogonal to a longitudinal centerline of the second connector 152 forming a 'T' shape with a body of the second connector 152. The pair of tabs 158 is configured to provide an additional point of leverage, if needed, when pushing or pulling the first connector 132 along the second connector 152 in accordance with the one-handed mechanism. For example, once the first connector 132 is inserted or otherwise seated in the second connector 152, a clinician can dispose his or her thumb behind the pair of tabs 158 and his or her index and middle fingers respectively behind a first and second tab of the pair of finger pads 142 and subsequently draw the first connector 132 and the second connector 152 together in a clamping motion. Depending upon the clinician's orientation, the clinician can use the same clamping motion with his or her thumb behind the first or second tab of the pair of finger pads 142 and his or her index and middle fingers respectively behind a first and second tab of the pair of tabs 158 and subsequently draw the first connector 132 and the second connector 152 together. The pair of tabs 158 is also configured to provide a palpable stop (under the drape) for the first connector 132, if needed, when pushing or pulling the first connector 132 along the second connector 152 in accordance with the one-handed mechanism.

Figure 6C:
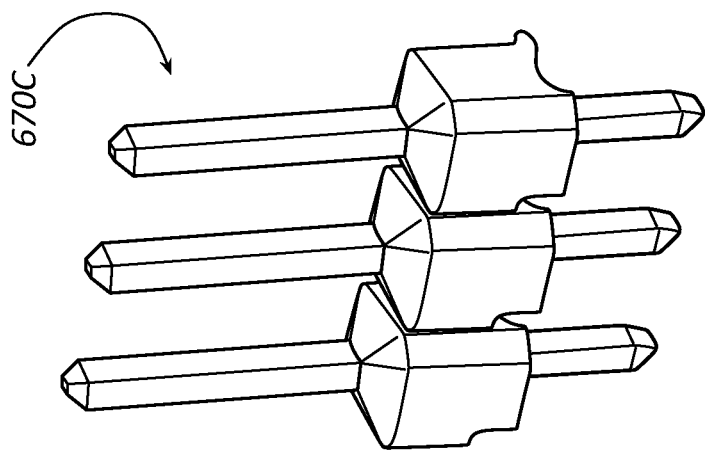
FIG. 6C illustrates a plurality of piercing elements in accordance with some embodiments.
Figure 6B:
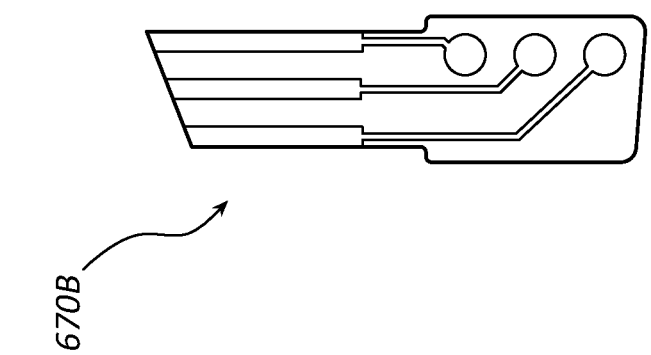
FIG. 6B illustrates a second piercing element in accordance with some embodiments.
Figure 6A:
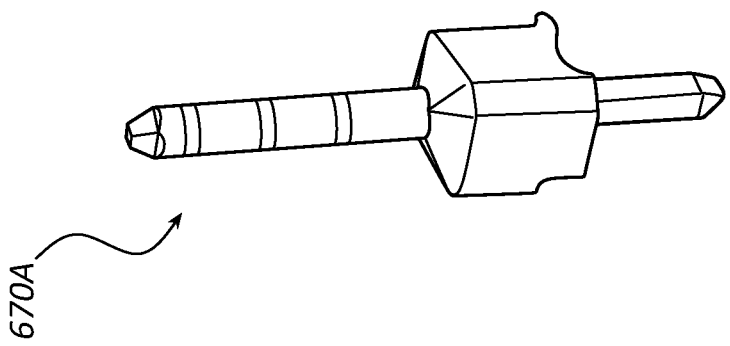
FIG. 6A illustrates a first piercing element in accordance with some embodiments.

FIGS. 6A-6C illustrate different piercing elements of the first connector 132 in accordance with some embodiments. The first connector 132 includes at least a first piercing element 170 (see FIG. 5B) configured to pierce a drape interposed between the second connector 152 (e.g., under a sterile drape in a non-sterile field) and the first connector 132 (e.g., over the sterile drape in a sterile field) such as pierce the drape from a sterile side of the drape. The first piercing element 170 has one or more electrical contacts. The second connector 152 includes a first receptacle such as the receptacle 160 (see FIG. 4) configured to receive the first piercing element 170 when inserted in the first receptacle. The first receptacle has one or more electrical contacts configured to form at least a first electrical connection of one or more electrical connections with the first connector 132 when the first piercing element 170 is inserted in the first receptacle.

As shown in FIG. 6A, the first piercing element 170 can be a jack plug 670A configured to make one or more electrical connections upon insertion into a complementary jack as the first receptacle (e.g., the receptacle 160) of the second connector 152. The jack plug 670A can be a tip-sleeve ("TS") jack plug with a needle-like tip electrical contact and a sleeve electrical contact. The jack plug 670A can be a tip-ring-sleeve ("TR$_n$S") jack plug with a needle-like tip, n ring electrical contacts with n≥1 (N), and a sleeve electrical contact. For example, the jack plug 670A of FIG. 6A is a TRRS jack plug having a needle-like tip electrical contact, two ring electrical contacts, and a sleeve electrical contact.

Figure 7:
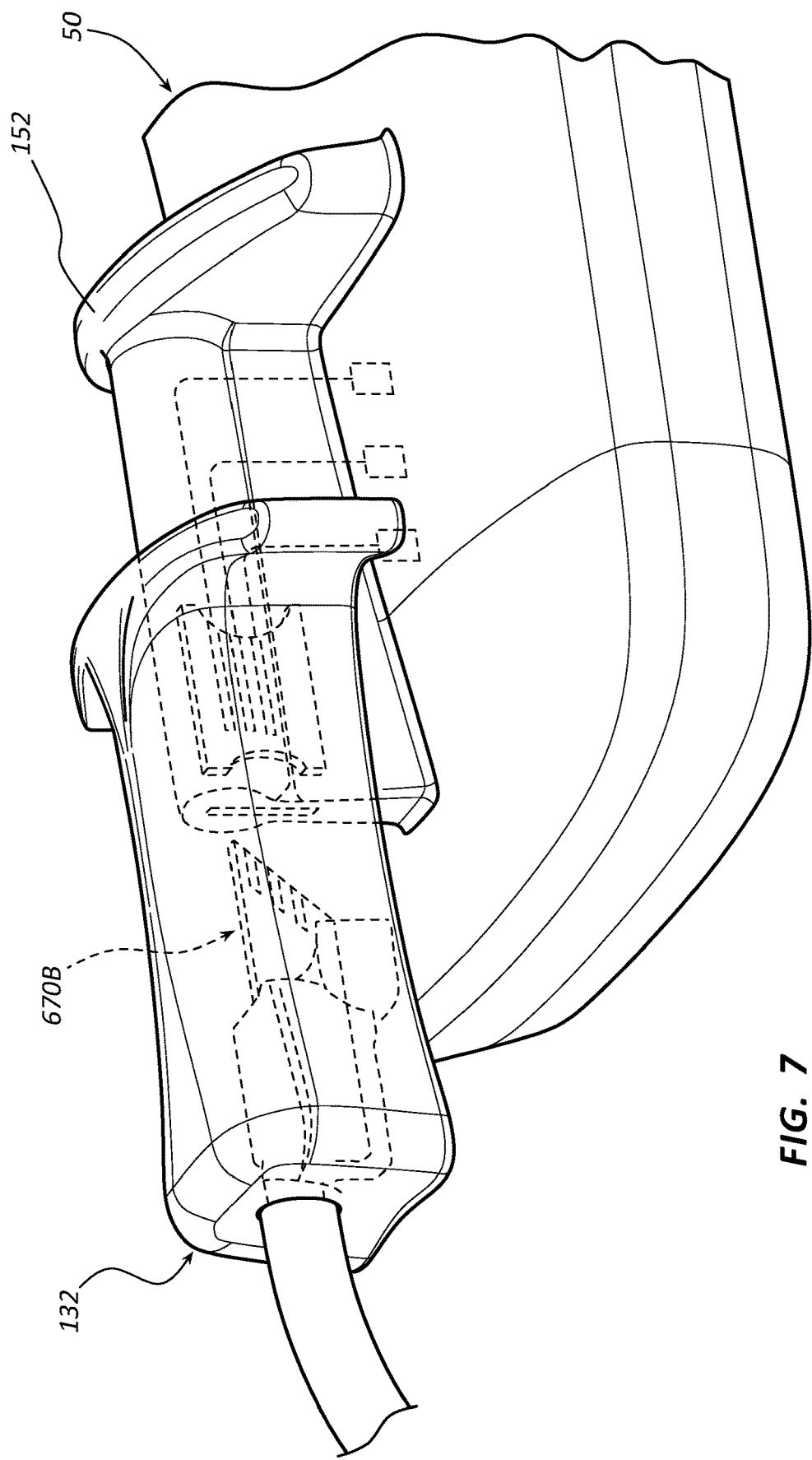
FIG. 7 illustrates a blade-like piercing element of a first connector configured to insert into a slot-shaped receptacle of a second connector in accordance with some embodiments.

As shown in FIG. 6B, the first piercing element 170 can be a blade-like piercing element 670B of an end portion of a printed circuit board having the one or more electrical contacts thereon. The blade-like piercing element 670B and the one or more electrical contacts thereon are configured to respectively make one or more electrical connections upon insertion into a complementary slot of the second connector 152 configured as the first receptacle (e.g., the receptacle 160). FIG. 7 illustrates the blade-like piercing element 670B of the first connector 132 configured to insert into a slot-shaped receptacle of the second connector 152. Each additional electrical contact on the printed circuit board can be configured to support an additional communication channel for data transfer between the first connector 132 and the second connector 152.

The first piercing element 170 can be accompanied by a second piercing element, a third piercing element, or even more piercing elements as shown in FIG. 6C by a plurality of piercing elements 670C. Each piercing element of the piercing elements 670C includes one or more electrical contacts. If the plurality of piercing elements 670C includes two piercing elements, a first piercing element (e.g., the piercing element 170) of the two piercing elements is configured to pierce a drape in a first location, and a second piercing element of the two piercing elements is configured to pierce the drape in a second location different than the first location. Likewise, if the plurality of piercing elements 670C includes three piercing elements, a first piercing element (e.g., the piercing element 170) of the three piercing elements is configured to pierce a drape in a first location, a second piercing element of the three piercing elements is configured to pierce the drape in a second location different than the first location, and a third piercing element of the three piercing elements is configured to pierce the drape in a third location different than the first and second locations. Each additional piercing element such as the foregoing second and third piercing elements can be configured to support an additional communication channel for data transfer between the first connector 132 and the second connector 152.

Figure 8:
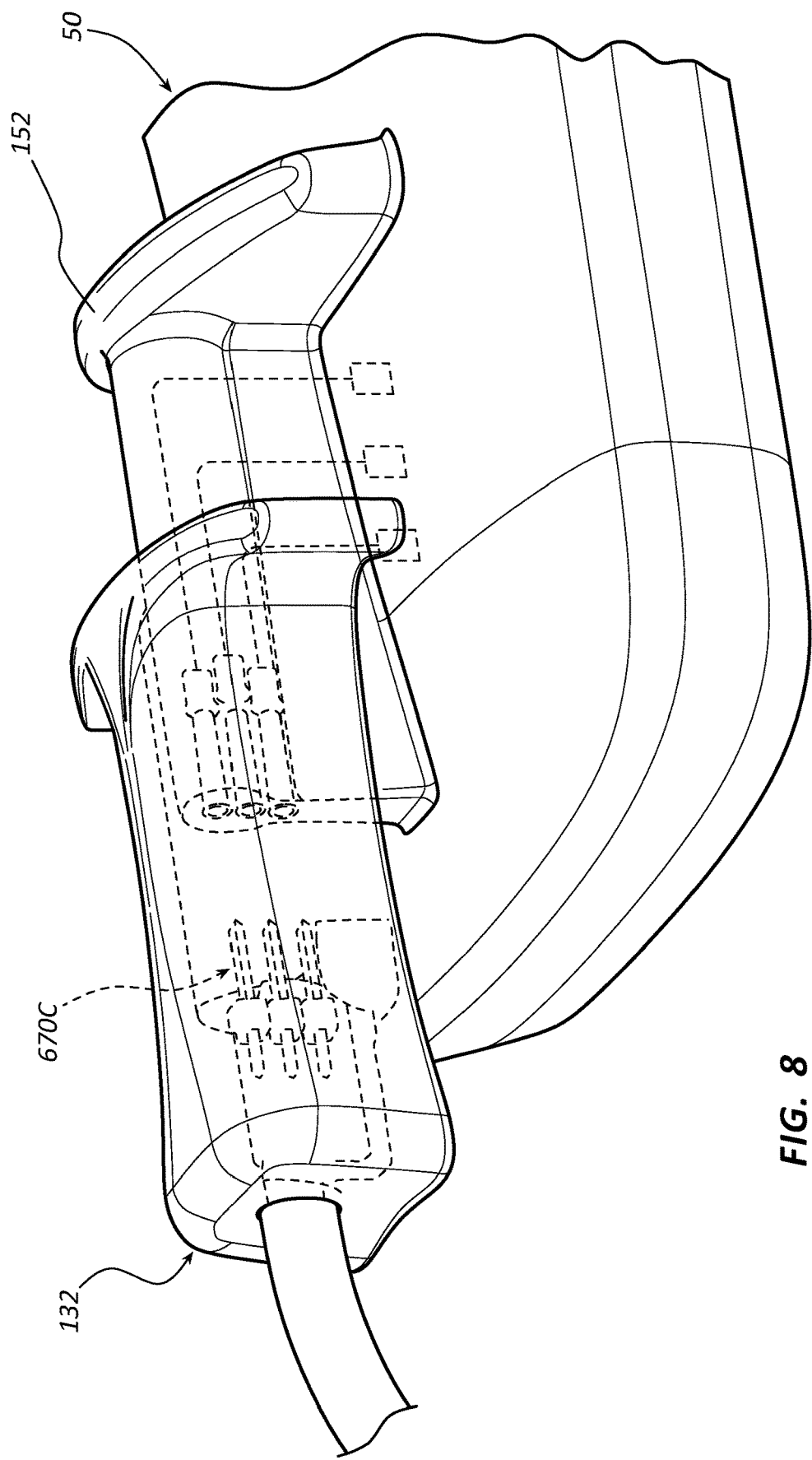
FIG. 8 illustrates a plurality of piercing elements of a first connector configured to insert into a plurality of receptacles of a second connector in accordance with some embodiments.

Again, each piercing element of the piercing elements 670C includes one or more electrical contacts. For each piercing element, the second connector 152 includes a complementary receptacle of a plurality of receptacles having one or more corresponding electrical contacts. As such, a first receptacle of the plurality or receptacles is configured to form a first electrical connection of one or more electrical connections when the first piercing element is inserted in the first receptacle, a second receptacle of the plurality or receptacles is configured to form a second electrical connection of the one or more electrical connections when the second piercing element is inserted in the second receptacle, a third receptacle of the plurality or receptacles is configured to form a third electrical connection of the one or more electrical connections when the third piercing element is inserted in the third receptacle, and so on. FIG. 8 illustrates the plurality of piercing elements 670C of the first connector 132 configured to insert into a plurality of receptacles of the second connector 152.

Figure 9C:
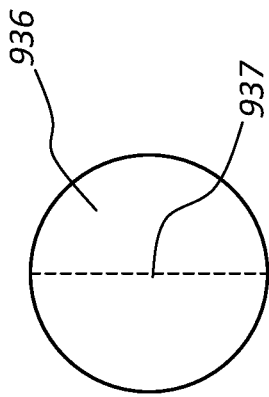
FIG. 9C illustrates a second drape seal in accordance with some embodiments.
Figure 9A:
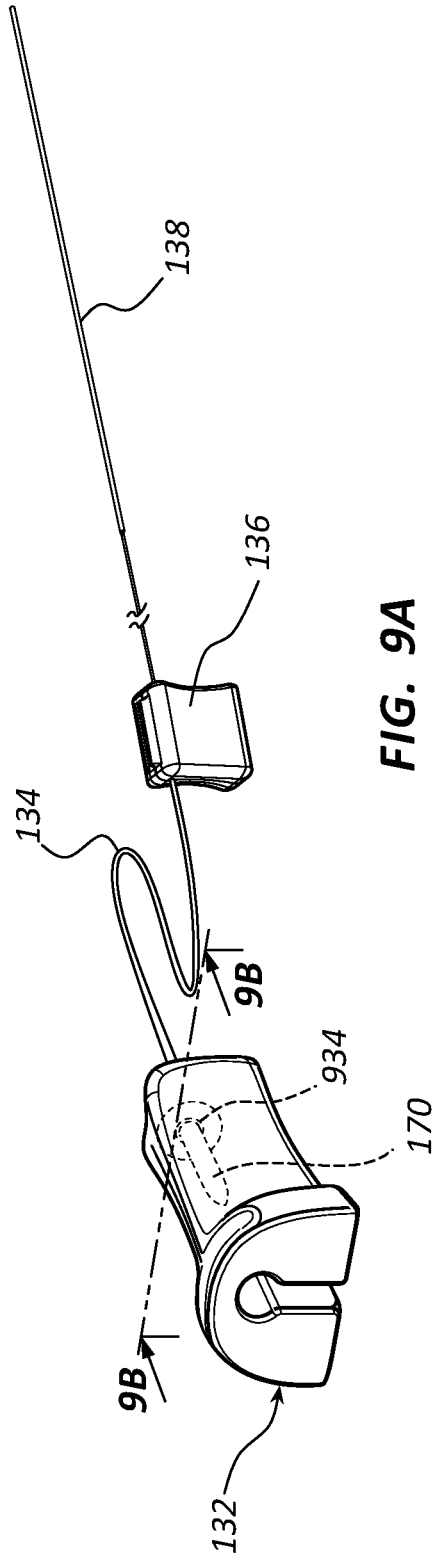
FIG. 9A illustrates a first connector including a first drape seal in accordance with some embodiments.
Figure 9B:
FIG. 9B illustrates a cross-section of the first connector of FIG. 9A including the drape seal.

FIG. 9A illustrates the first connector 132 including a drape seal 934 in accordance with some embodiments. FIG. 9B illustrates a cross-section of the first connector 132 including the drape seal 934. FIG. 9C illustrates a scored drape seal 936 in accordance with some embodiments.

As shown, the connection system 100 can further include the drape seal 934, which is configured to adhere to a drape about one or more piercings in the drape respectively by one or more piercing elements. The drape seal 934 is configured as a sticker with adhesive on at least its distal face (e.g., adhesive over the entire distal face, adhesive around a perimeter of the distal face, etc.) disposed within the first connector 132 around a proximal-end portion of the piercing element 170, 670A, 670B or the plurality of piercing elements 670C. The drape seal 934 can be any shape including the disk shape shown in FIGS. 9A-9C. The drape seal 934 is a self-scaling polymer septum, the polymer including, but not limited to, natural rubber, synthetic rubber, silicon rubber, polytetrafluoroethylene, or a combination thereof. The compressive nature of the self-scaling polymer septum around the proximal-end portion of the piercing element 170, 670A, 670B or the plurality of piercing elements 670C holds the drape seal 934 in place in the first connector 132 until the drape seal 934 is pulled away from the first connector 132. Upon mechanically coupling and electrically connecting the first connector 132 and the second connector 152 with a drape interposed therebetween, the distal face of the drape seal 934 adheres to the drape about the one or more piercings. The drape seal 934 is configured to remain adhered to the drape and selectively pull away from the first connector 132 when the first connector 132 and the second connector 152 are disconnected, thereby sealing the drape. Thus, the drape seal 934 preserves the sterile field provided by the drape upon disconnection of the connection system 100.

Instead of the drape seal 934, the scored drape seal 936 can be used. The scored drape seal 936 is like the drape seal 934, but the scored drape seal 936 includes a score 937 configured to allow the piercing element 170, 670A, 670B or the plurality of piercing elements 670C therethrough. Such a score can be advantageous when the piercing element 670B or the plurality of piercing elements 670C is present in the first connector 132. This is because the foregoing piercing elements have more surface area than either the piercing element 170 or the piercing element 670A. The greater the surface area of the piercing element, the greater the resistance to pulling the drape seal from its position about the piercing element. Thus, without the score 937 in certain embodiments, the adhesive or the drape itself might not be strong enough to pull the piercing element from its position about the piercing element.

A method of establishing one or more electrical connections through a drape with the connection system 100 includes placing the drape over the second connector 152; aligning the alignment protrusion 140 (or the pair of alignment protrusions) within a distal-end portion of the first connector 136 with the alignment notch 154 (or the pair of alignment notches) in a medial portion of the second connector 152; disposing the first connector 136 over the second connector 152 with the drape interposed between the first connector 136 and the second connector 152, the drape self-tightening over the second connector 152 while disposing the first connector 136 over the second connector 152; sliding the alignment protrusion 140 (or the pair of alignment protrusions) of the first connector 136 along the channel 156 (or the pair of channels) with the drape between the alignment protrusion 140 (or the pair of alignment protrusions) and the channel 156 (or the pair of channels); piercing a sterile side of the drape with the piercing element 170, 670A, 670B (or the piercing elements 670C) of the first connector 136, the piercing element 170, 670A, 670B (or the piercing elements 670C) having one or more electrical contacts; inserting the piercing element 170, 670A, 670B (or the piercing elements 670C) into the receptacle 160 of the second connector 152, the receptacle 160 having one or more electrical contacts; and forming the one or more electrical connections respectively between the one or more electrical contacts of the piercing element 170, 670A, 670B (or the piercing elements 670C) and the one or more electrical contacts of the receptacle 160.

The method can further include viewing the disposing of the first connector 136 over the second connector 152 and the sliding of the first connector 136 along the second connector 152 through the first connector 136, wherein the first connector 132 is transparent for the viewing through the first connector 136.

The method can further include sealing the drape with the drape seal 934, 936, wherein the drape seal 934, 936 is a self-sealing polymer septum disposed within the first connector 136 around a proximal-end portion of the piercing element the piercing element 170, 670A, 670B (or the piercing elements 670C).

The method can further include confirming success in forming the one or more electrical connections by a change from a first state of the LED 184 on the first connector 132 to a second state of the LED 184 upon forming the one or more electrical connections.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A method of assembling a catheter placement system, the method comprising:
providing a location sensor configured for placement on a patient, the location sensor comprising:
an exterior channel having a channel length;
an exterior alignment notch positioned above the exterior channel, the exterior alignment notch having a notch length less than the channel length; and
an interior receptacle including an electrical contact;
providing a drape configured to cover the patient and the location sensor; and
providing a connector tethered to a catheter tracking element, the connector comprising an alignment protrusion and a piercing element having an electrical contact, the connector configured to couple to the location sensor through the drape, wherein:
the alignment protrusion of the connector is configured to move through the exterior alignment notch and into the exterior channel when the connector is pressed vertically over the location sensor, and
the piercing element is configured to pierce the drape and form an electrical connection with the electrical contact in the interior receptacle when the connector is slid horizontally over the location sensor such that the alignment protrusion slides along the exterior alignment notch.

2. The method of claim 1, wherein the piercing element of the connector is a jack plug having a needle-like tip electrical contact, one or more ring electrical contacts, and a sleeve electrical contact, and wherein the interior receptacle includes a jack having complementary electrical contacts.

3. The method of claim 1, wherein the piercing element of the connector is a blade-like end portion of a printed circuit board, and the interior receptacle includes a slot having complementary electrical contacts.

4. The method of claim 1, wherein the connector further comprises a seal disposed around a proximal-end portion of the piercing element.

5. The method of claim 4, wherein the seal is a self-sealing polymer septum.

6. The method of claim 1, wherein the location sensor comprises a plurality of interior receptacles, wherein the connector comprises a plurality of piercing elements, and wherein the plurality of interior receptacles are configured to receive the plurality of piercing elements when the connector is slid horizontally over the location sensor.

7. The method of claim 6, wherein the connector further comprises a seal disposed around a proximal-end portion of each of the plurality of piercing elements.

8. The method of claim 1, wherein the connector further comprises a light-emitting diode ("LED") configured to change from a first state to a second state, wherein the LED is configured to be in the first state prior to the piercing element forming the electrical connection with the electrical contact in the interior receptacle, and wherein the LED is configured to change to the second state when the piercing element forms the electrical connection with the electrical contact in the interior receptacle.

9. The method of claim 8, wherein the LED is configured to change from the first state to the second state when a dedicated LED circuit is completed.

10. The method of claim 1, wherein the connector includes a pair of finger pads.

11. The method of claim 1, wherein the connector is configured to couple to the location sensor through the drape to tighten the drape without bunching when the alignment protrusion moves through the exterior alignment notch and into the exterior channel.

12. The method of claim 1, wherein the connector includes a transparent cover surrounding the piercing element.

13. The method of claim 1, wherein the location sensor includes a fin connector, the fin connector including the exterior channel, the exterior alignment notch, and the interior receptacle.

14. The method of claim 13, wherein the exterior channel, the exterior alignment notch, and the interior receptacle are on one side of the fin connector, and wherein an opposing side of the fin connector comprises an opposing exterior channel and an opposing alignment notch.

* * * * *